(12) United States Patent
Nisnevich et al.

(10) Patent No.: US 7,217,825 B2
(45) Date of Patent: May 15, 2007

(54) SYNTHESIS OF IRBESARTAN

(75) Inventors: Gennady Nisnevich, Haifa (IL); Igor Rukhman, Haifa (IL); Boris Pertsikov, Nesher (IL); Julia Kaftanov, Haifa (IL); Ben-Zion Dolitzky, Petach Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/348,945

(22) Filed: Feb. 6, 2006

(65) Prior Publication Data

US 2006/0135544 A1    Jun. 22, 2006

Related U.S. Application Data

(62) Division of application No. 10/759,906, filed on Jan. 16, 2004, now Pat. No. 7,019,148.

(60) Provisional application No. 60/440,997, filed on Jan. 16, 2003.

(51) Int. Cl.
 *C07D 257/04* (2006.01)
 *C07D 235/02* (2006.01)

(52) U.S. Cl. .................... 548/253; 548/300.7

(58) Field of Classification Search ............. 548/253, 548/300.7
See application file for complete search history.

(56) References Cited

U.S. PATENT DOCUMENTS 5,270,317 A    12/1993  Bernhart et al.
5,310,929 A    5/1994   Ardecky et al.
5,541,209 A    7/1996   Spinale et al.
5,559,233 A    9/1996   Bernhart et al.
5,629,331 A    5/1997   Caron et al.

FOREIGN PATENT DOCUMENTS

| EP | 0 508 393 A | 10/1992 |
| EP | 0 782 996 A | 7/1997 |
| FR | 2 780 403 A | 12/1999 |
| GB | 2 281 072 A | 2/1995 |
| WO | WO 94/11012 A | 5/1994 |
| WO | WO 2004/007482 A | 1/2004 |

OTHER PUBLICATIONS

N. Miyaura et al., "A New Stereospecific Cross-Coupling by the Palladium-Catalyzed Reaction of 1-Alkenylboranes with 1-Alkenyl or 1-Alkynyl Halides," Tetrahedron Letters, No. 36, 1979, p. 3437-3440.

N. Miyaura, A. Suzuki, "Stereoselective Synthesis of Arylated (E)-Alkenes by the Reaction of Alk-1-enylboranes with Aryl Halides in the Presence of Palladium Catalyst", J.C.S. Chem Commun. 1979, pp. 866-867.

Murugesan, Natesan, et al., "Discovery Of N-Isoxazolyl Biphenylsulfonamides As Potent Dual Angiotensin II And Endothelin A Receptor Antagonists", *J. of Med. Chem.* (2002), 45(18), 3829-3835.

Bernhart C.A., et al., "A New Series of Imidazolones: Highly Specific and Potent Nonpeptide $AT_1$ Antiotensin II Receptor Antagonists", *J. of Med. Chem.* vol. 36, No. 22, 1993, pp. 3371-3380.

*Primary Examiner*—Kamal A. Saeed
*Assistant Examiner*—Shawquia Young
(74) *Attorney, Agent, or Firm*—Kenyon & Kenyon LLP

(57) ABSTRACT

Provided are a method of making irbesartan via a Suzuki coupling reaction and a novel intermediate, 2-butyl-3-(4'-bromobenzyl)-1,3-diazaspiro[4.4]non-1-ene-4-one, for such process. The novel process includes the step of reacting such intermediate with a protected imidazolephenylboronic acid.

12 Claims, No Drawings

SYNTHESIS OF IRBESARTAN

RELATED APPLICATIONS

The present invention relates to a novel synthesis of irbesartan.

This application is a divisional of U.S. patent application Ser. No. 10/759,906, filed Jan. 16, 2004 now U.S. Pat. No. 7,019,148, which claims the benefit of U.S. provisional application Ser. No. 60/440,997, filed Jan. 16, 2003, the contents of which are incorporated herein.

BACKGROUND OF THE INVENTION

Irbesartan is a known angiotensin II receptor antagonist (blocker). Angiotensin is an important participant in the renin-angiotensin-aldosterone system (RAAS) and has a strong influence on blood pressure. The structure of irbesartan is shown below (I).

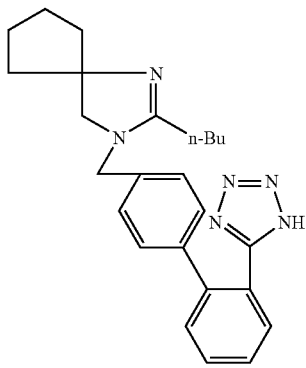

(I)

The synthesis of irbesartan is discussed, inter alia, in U.S. Pat. Nos. 5,270,317 and 5,559,233; both of which are incorporated herein in their entirety by reference. In the synthesis therein disclosed, the prepenultimate reaction step (exclusive of work-up and purification) involves the reaction of a cyano group on the biphenyl ring with an azide, for example tributyltin azide. Reaction time as long as 210 hours can be required. See, e.g., '317 patent.

U.S. Pat. No. 5,629,331 also discloses a synthesis of irbesartan from a precursor 2-n-butyl-3-[(2'-cyanobiphenyl-4-yl)methyl]-1,3-diazaspiro[4.4]non-1-ene-4one with sodium azide using a dipolar aprotic solvent. As acknowledged in the '331 patent, there are safety risks involved in the use of azides (column 4, line 39). Also, dipolar aprotic solvents (e.g. methyl pyrrolidone) are relatively high boiling and can be difficult to remove.

There is a need for an improved synthetic route to irbesartan.

SUMMARY OF THE INVENTION

In one aspect, the present invention relates to a method of making 2-butyl-3-[[2'-(1-trityl-1H-tetrazol-5-yl)biphen-4-yl]methyl]1,3-diazaspiro[4.4]non-1-ene-4-one (IRB-03) including the steps of reacting 2-butyl-3-(4'-bromophenyl)-1,3-diazaspiro[4.4]non-1-ene-4-one (IRB-05) with 2-(1-trityl-1H-tetrazol-5-yl)phenylboronic acid (IRB-07) in the presence of a first solvent, especially tetrahydrofuran (THF) or dimethoxyethane, a second solvent, especially water, particularly combined with a base, and a catalyst that includes especially a palladium complex, e.g., Pd(O(O)CCH₃)₂ and a phosphine, especially a triarylphosphine, e.g. triphenyl phosphine (PPh₃).

In another aspect, the present invention relates to a process for making a 3-(haloaryl)-1,3-diazaspiro[4.4]non-1-ene-4-one compound, especially 3-(4'-bromobenzyl)-1,3-diazaspiro[4.4]non-1-ene-4-one, including the step of reacting (combining), in the presence of a phase transfer catalyst (e.g. tetrabutylammonium sulfate), an acid addition salt, especially a hydrochloride, of 1,3-diazaspiro[4.4]non-1-ene-4-one with a haloaryl compound, especially a bromobenzyl halide compound (e.g. 4-bromobenzyl), in a solvent system including a first solvent, especially an aromatic hydrocarbon, and a second solvent, especially brine containing a base.

In another aspect, the present invention relates to the compound 2-butyl-3-(4'-bromobenzyl)-1,3-diazaspiro[4.4]non-1-ene-4-one, especially when prepared according to the forgoing process.

In still a further aspect, the present invention relates to a method of making a 5-phenyl-1-trityl-1H-tetrazole compound including the step of reacting 5-phenyl-1-H-tetrazole with chlorotriphenylmethane (trityl chloride) in a solvent, especially tetrahydrofuran, in the presence of a base, especially triethylamine.

In yet another aspect, the present invention relates to a method of making 2-(tetrazol-5-yl)phenylboronic acid including the step of reacting 5-phenyl-1-trityl-1H-tetrazole with a borate, especially a trialkyl borate (e.g. tri-isopropyl borate) in a solvent, especially tetrahydrofuran, and in the presence of a base, especially n-butyllithium.

In still yet another aspect, the present invention relates to a method of making irbesartan that includes the step of reacting 2-butyl-3-(4'bromobenzyl)-1,3-diazaspiro[4.4]non-1-ene-4-one with 2(1-trityl-1H-tetrazol-5-yl)phenylboronic acid in a two-phase solvent system having a first solvent, especially THF or dimethoxyethane or a mixture of these, and a second solvent, especially water, in the presence of a catalyst, especially a palladium complex or a nickel complex.

In a further aspect, the present invention relates to a process of making irbesartan that includes the step of reacting an acid addition salt, especially the hydrochloride, of 2-butyl-1,3-diazaspiro[4.4]non-1-ene-4-one with a haloaryl compound, especially 4-bromobenzyl bromide in the presence of a base, especially KOH or NaOH, in a two-phase solvent system having a first solvent, especially toluene, and a second solvent, especially water or brine.

DETAILED DESCRIPTION OF THE INVENTION

The present invention provides a novel synthesis of irbesartan and analogues thereof, including the step of reacting a 2-(5-tetrazoyl)phenylboronic acid with a 3-(haloaryl)-1,3-diazaspiro[4.4]non-1-ene-4-one. The step is carried out in the presence of a palladium or nickel catalyst. Such a synthetic step is known by one of skill in the art as a Suzuki coupling reaction. See, e.g., N. Miyaura et al., Tetrahedron Letters 1979, 3437. See also, N. Miyaura, A. Suzuki, Chem. Commun. 1979, 866. The step can be carried out in a two-phase reaction system having first and second liquid phases.

The first and second phases include first and second solvents, respectively, which are substantially immiscible in each other so that, when combined in a reaction vessel, a two-phase system is formed. Solvents are substantially immiscible in each other when equal volumes of them are mixed together, a two-phase system is formed in which the volume of the two phases is essentially equal. Preferably, substantially immiscible solvents are soluble in each other to the extent of about 1% (weight basis) or less.

The first solvents are organic solvents. Examples of preferred organic solvents include, but are not limited to: ether solvents such as 1,2-dimethoxyethane (DME), diethoxymethane, (glymes), and tetrahydrofuran (THF); formals such as diethyl formal; and hydrocarbon solvents such as, toluene, m-xylene, o-xylene, the tetralins; and mixtures of any of the foregoing. Other hydrocarbons useful as first solvents in the practice of the present invention will be apparent to the skilled artisan. Diethyl formal is the preferred formal. 1,2-dimethoxyethane (DME) is the preferred glyme and is particularly preferred as an ether first solvent, especially in combination with THF when the catalyst includes a palladium complex.

The second solvent can be water, or, preferably, an inorganic base combined with water. When an inorganic base is used, the preferred inorganic base is potassium carbonate. Potassium hydroxide and sodium hydroxide are other examples of inorganic bases.

The novel synthesis of irbesartan, and analogues thereof, of the present invention includes the step of reacting a protected (e.g. tritylated) 2-(5-tetrazoyl)phenylboronic acid with a 3-haloaryl-1,3diazaspiro[4.4]non-1-ene-4-one. A preferred 2-(5-tetrazoyl)phenylboronic acid is 2-(5-(1-trityl-1H-tetrazole))phenylboron acid (IRB-07), Structure II. A preferred 3-haloaryl-1,3-diazaspiro[4.4]non-1-ene-3-4-one is 2-butyl-3-(4'-bromobenzyl)-1,3-diazaspiro[4.4]non-1-ene-3-one (IRB-05), Structure III.

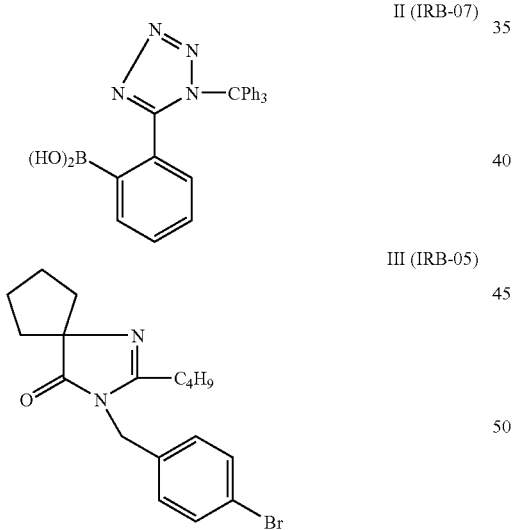

The step is carried out in a two-phase reaction system having first and second liquid phases.

A catalyst is combined with the first liquid phase, preferably including an ether solvent. Any known catalyst for the Suzuki reaction can be used. Preferably, the catalyst is selected from palladium and nickel complexes. Most preferred catalysts include $Pd(O(O)CCH_3)_2$, $PdCl_2$ and $NiCl_2$. When a palladium complex such as $Pd(O(O)CCH_3)_2$ [e.g. $PdOAc_2$] is used, the catalyst also includes a triaryl phosphine, especially triphenyl phosphine. When the catalyst includes a palladium complex, the first solvent preferably includes an ether solvent, like DME, that can form a complex with Pd.

As described above, the first liquid phase is an organic solvent phase, most preferably and particularly when the catalyst includes a palladium complex, the first liquid phase is a mixture of 1,2-dimethoxyethane and THF. The ratio of 1,2-dimethoxyethane: THF can be from about 10:1 to about 1:5, the most preferred ratio of 1,2-dimethoxyethane: THF is from about 6:1 to about 2:1. The reaction is carried out in the presence of a catalyst.

Subsequently, IRB-07 is combined with the solvent mixture. Water, a base, and IRB-05 are added, preferentially sequentially, to the reaction mixture, and a two-phase reaction system having a first organic solvent phase and a second aqueous phase is formed. The reaction mixture is heated under reflux conditions for a reaction time of between 2 to 4 hours.

After the reaction time, the reaction mixture is allowed to cool, and the two phases are separated. If desired, the aqueous phase can be extracted one or more times with toluene and the extract(s) combined with the first (aromatic hydrocarbon) phase. The first phase is evaporated to obtain crude residue of product IRB-03.

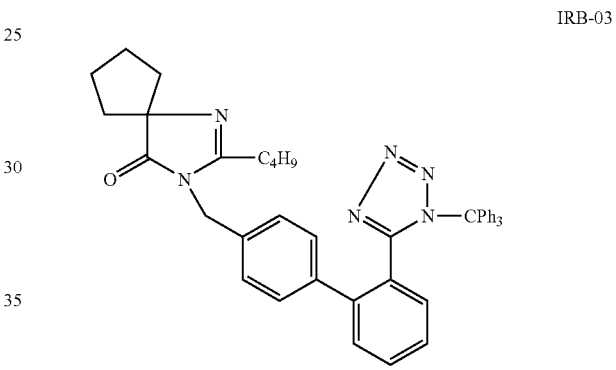

In embodiments in which 2-(1-trityl-1H-tetrazol-5-yl) phenylboronic acid, (IRB-07), is the phenylboronic acid, the synthetic method of the present invention can and preferably does include a further step in which the trityl group is cleaved from the tetrazole ring to produce irbesartan (IRB-00), or an analogue thereof. Crude residue produced in the synthetic step described above is dissolved in a suitable water-miscible solvent. A solvent is water miscible if it is miscible with water at least in any proportion from 80:20 to 20:80 (weight basis). Acetone is a preferred water-miscible solvent. The resulting solution is acidified and agitated at a temperature between about 15° C. and about 30° C. The time of the cleavage reaction can be conveniently monitored using thin layer chromatography. The acid is neutralized with a molar excess of base, preferably aqueous KOH or NaOH, and the water-miscible solvent is evaporated, preferably at reduced pressure. The trityl alcohol formed is separated and the liquid phase is acidified (e.g. to a pH of about 4), preferably with mineral acid, most preferably with HCl or $H_2SO_4$. The resulting suspension is cooled and the product recovered by, for example, filtration. If desired, the isolated product can be washed with an organic solvent, preferably a lower aliphatic alcohol, most preferably isopropanol or butanol, and dried, preferably at reduced pressure.

The 2-(5-tetrazoyl)phenylboronic acid and 1,3-diazaspiro [4.4]non-1-ene-3-(haloaryl)-4-one which are reacted in the method of the present invention to produce irbesartan or an analogue thereof, can be prepared by methods known in the art, or by the following synthetic procedures.

The 2-(tetrazol-5-yl)phenylboronic acid can be prepared by first reacting a 5-phenyl-1H-tetrazole with chlorotriphenylmethane in the prresence of a base, especially an amine (e.g. triethylamine) in a suitable solvent system to provide a 5-phenyl-1-trityl-1H-tetrazole. A preferred 5-phenyl-1-trityl-1H-tetrazole is IRB-06 (structure shown in Examples). Suitable solvents for the solvent system include organic solvents. A particularly preferred solvent system is a mixture of THF and triethyl amine as the base. Following removal of by-products, the 5-phenyl-1-trityl-1H-tetrazole, such as IRB-06, can be isolated prior to use in the next step of the synthesis, or used in solution form. The protected tetrazole so formed is subsequently reacted with a suitable borate in the presence of a base, to form the desired boronic acid derivative, such as 2-(1-trityl-1H-tetrazol-5-yl)phenylboronic acid (IRB-07; structure shown in Examples). The reaction is carried out in solution, preferably in an organic solvent. The organic solvent is most preferably THF. Suitable bases will be apparent to the skilled artisan. A preferred base is butyllithium. The preparation can be at any suitable temperature, preferably at a temperature lower than about −20° C. The reaction is allowed to proceed for a time that the skilled artisan will know to adjust according to the reaction temperature.

The 3-haloaryl-1,3-diazaspiro[4.4]non-1-ene-4-one can be prepared by combining a 1,3-diazaspiro[4.4]non-1-ene-4-one acid addition salt, preferably a hydrochloride salt, with a haloaryl compound. A preferred 1,3-diazaspiro[4.4]non-1-ene-4-one acid addition salt is 2-butyl-1,3-diazaspiro[4.4]non-1-ene-4-one hydrochloride (IRB-01). A preferred haloaryl compound is 4-bromobenzyl bromide. Reaction of 2-butyl-1,3-diazaspiro [4.4]non-1-ene-4-one hydrochloride (IRB-01) with 4-bromobenzyl bromide leads to the production of 2-butyl-3-(4'-bromobenzyl)-1,3-diazaspiro[4.4]non-1-ene-4-one (IRB-05). 2-Butyl-1,3-diazaspiro[4.4]non-1-ene-4-one is known in the art and is disclosed, for example, in U.S. Pat. No. 5,559,233, which is incorporated herein by reference.

The reaction is carried out in a two-phase reaction system having first and second liquid phases.

A first liquid phase comprising the haloaryl compound and a phase transfer catalyst in a suitable solvent is prepared. The solvent may be an organic solvent. A most preferred solvent is toluene.

Phase transfer catalysts are well known to one skilled in the art of organic synthesis. Phase transfer catalysts are of particular utility when at least first and second compounds to be reacted with each other have such different solubility characteristics that there is no practical common solvent for them and, accordingly, combining a solvent for one of them with a solvent for the other of them results in a two-phase system.

Typically, when such compounds are to be reacted, the first reactant is dissolved in a first solvent and the second reactant is dissolved in a second solvent. Because the solvent for the first reactant is essentially insoluble in the solvent for the second reactant, a two-phase system is formed and reaction occurs at the interface between the two phases. The rate of such an interfacial reaction can be greatly increased by use of a phase transfer catalyst (PTC).

Several classes of compounds are known to be capable of acting as phase transfer catalysts, for example quaternary ammonium compounds and phosphonium compounds, to mention just two. Tetrabutylaminonium hydrogensulfate is a preferred PTC for use in the practice of present invention.

A second liquid phase comprising a 1,3-diazaspiro[4.4]non-1-ene-4-one acid addition salt, water and a base, preferably an inorganic base, most preferably, KOH. The base is present in an amount between about 1 and about 6 molar equivalents relative to the number of moles of 1,3-diazaspiro[4.4]non-1-ene-4-one acid salt.

The first and second solutions are combined to form a reaction system (mixture) that has first and second phases. The combining can be in any suitable vessel that is equipped with means for vigorous agitation of the reaction system to maximize the interfacial area between the two phases. The combining can be at any temperature from about 20° C. to about 95° C., preferably at about 90° C. The reaction is allowed to proceed in the two phase system for a time that the skilled artisan will known to adjust according to the reaction temperature. When the reaction temperature is about 90° C., a reaction time between about 1 and about 2 hours is usually sufficient.

After the reaction time, the reaction system is allowed to cool, the two phases are separated. If desired, the aqueous phase can be extracted one or more times with toluene and the extract(s) combined with the first (aromatic hydrocarbon) phase. The first phase is evaporated to obtain crude residue.

The present invention can be illustrated in one of its embodiments by the following non-limiting example.

EXAMPLE IA

Preparation of IRB-05

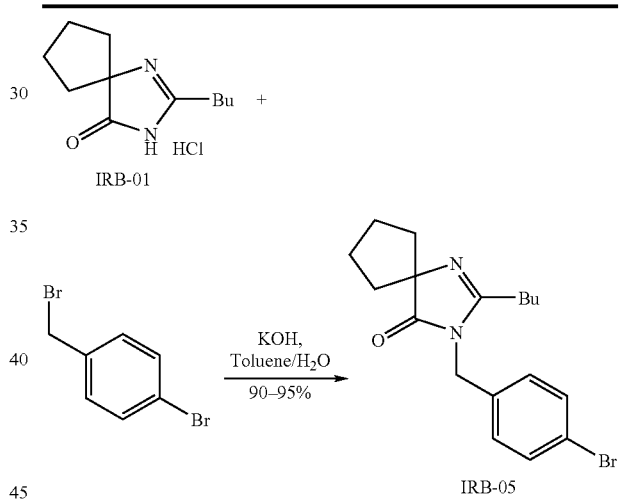

|  | Mw | Weight; volume | Mmol | Eq. |
|---|---|---|---|---|
| IRB-01 | 230.73 | 57.7 g | 250 | 1.25 |
| 4-Bromobenzyl bromide | 249.49 | 50.0 g | 200 | 1.0 |
| Potassium hydroxide, 85% | 56.11 | 49.6 g | 750 | 3.75 |
| Water |  | 200 mL |  |  |
| Bu$_4$NHSO$_4$ | 339.54 | 8.5 g |  | 0.125 |
| Toluene |  | 800 mL |  |  |

To a preheated (90° C.) solution of 4-bromobenzyl bromide and phase transfer catalyst (Bu$_4$NHSO$_4$) in toluene was added a prestirred (40 min at room temperature) solution of KOH and IRB-01 in water. The resulting two-phase mixture was heated for 1 hour at 90° C. with vigorous stirring. The mixture was cooled to room temperature, water (500 mL) was added and the mixture was stirred for additional 30 min. The phases were separated and the aqueous phase was extracted with an additional portion of toluene (100 mL). The combined organic portions were washed with water and brine, dried over Na$_2$SO$_4$ and evaporated under reduced pressure. 74.0 g of IRB-05 was obtained as a colorless oil. The yield was 94%, with a purity of 94%.

EXAMPLE 1B

Preparation of IRB-06

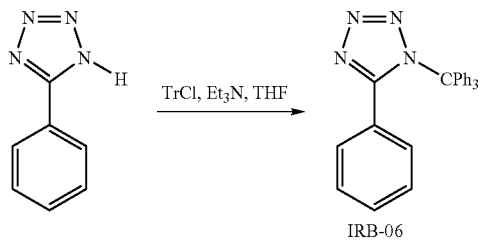

| | Mw | Weight; volume | Mmol | Eq. |
|---|---|---|---|---|
| 5-Phenyl-1H-tetrazol | 146.15 | 56.0 g | 383 | 1.0 |
| Chlorotriphenylmethane | 278.78 | 112.0 g | 402 | 1.05 |
| Et$_3$N | 101.2 | 61.0 ml, | 440 | 1.15 |
| THF | | 400 mL | | |

To a solution of 5-phenyl-1H-tetrazol and triethylamine in dry THF was added, in one portion, chlorotriphenylmethane. The reaction was slightly exothermic, about 40° C. The resulting suspension was stirred under argon for 2 hours (TLC monitoring; Hex/EtOAc 4:1). The mixture was cooled to 0° C., stirred for 30 min and the precipitated triethylammonium chloride was filtered and washed with cold THF (100 mL). The filtrate was evaporated under reduced pressure and the yellow solid residue (approx. 180 g) was crystallized from acetonitrile (800 mL) to give 141.5 g. The yield was 94%, with a purity of 94%.

EXAMPLE 1C

Preparation of 2-(5-(1-trityl-1H-tetrazol)phenylboronic acid (IRB-07)

| | Mw | Weight, volume | mmol | Eq. |
|---|---|---|---|---|
| IRB-06 | 388.46 | 39.0 g | 100 | 1.0 |
| BuLi (1.6 M in hexane) | | 75.0 mL | 120 | 1.2 |
| Triisopropyl borate | 188.08 | 30.0 mL | 130 | 1.3 |
| THF | | 250 mL | | |

The solution of 5-phenyl-1-trityl-1H-tetrazole (IRB-06) in dry THF (Prepared in Example 1B) was cooled to −20° C. under Argon. Traces of water were quenched with n-butyllithium (approx. 5 mL). When the mixture remained red for 5 minutes the addition was stopped. The main charge of n-butyllithium was then added dropwise at temperature below −15° C. and the resulting red suspension was stirred for additional 30 minutes at −20° C. The mixture was cooled to −30° C., and triisopropyl borate was slowly added, with the reaction temperature maintained at below −20° C. At this point, the slurry was dissolved and the resulting red solution was stirred for 30 minutes at −25° C., and then warmed to room temperature over 40 minutes. The solvents were evaporated under reduced pressure and the yellow semisolid residue was extracted with isopropyl alcohol (IPA) (200 mL) and cooled to 0° C. Saturated aqueous NH$_4$Cl (40 mL, approx. 180 mmol) was slowly added, keeping the temperature below 10° C., and the slurry of boronic acid was warmed to room temperature. Water (160 mL) was added over 20 minutes, and the resulting suspension was stirred for 2 hours at room temperature. The solid was filtered, washed with IPA/H$_2$O/Et$_3$N 50:50:2 (2×50 mL) and dried under reduced pressure at 40° C. until constant weight to give 47.0 g of IRB-07 as the 1:0.5 THF-H$_2$O solvate (off-white solid) that was used without additional purifications. The yield was 92%, with a purity of 94.5%.

EXAMPLE 1D

Preparation of 2-butyl-3-[2'-(triphenylmethyltetrazol-5-yl)-biphenyl-4-yl methyl]-1,3-diazaspiro[4.4]non-1-ene-4-one (IRB-03)

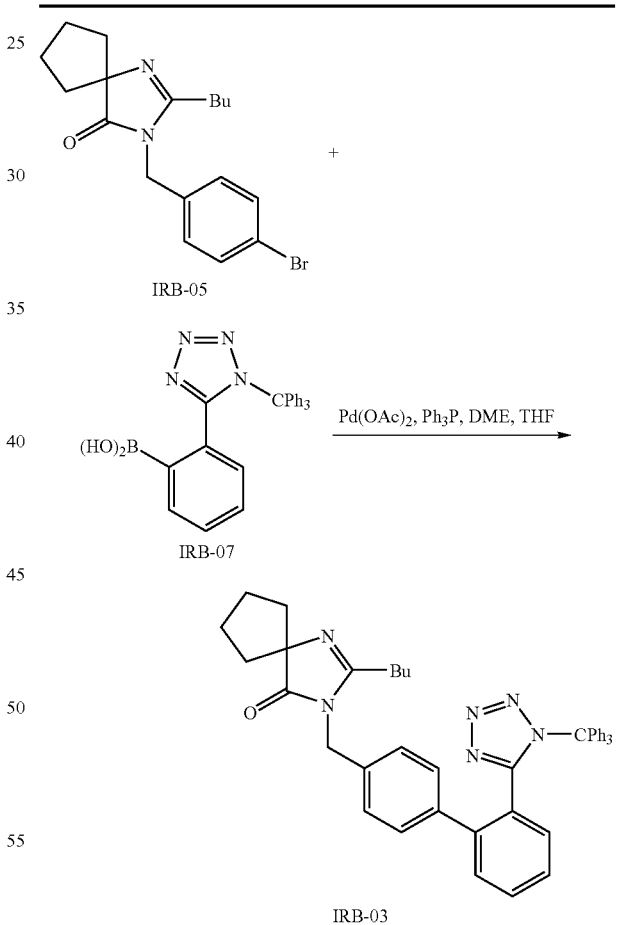

| | Mw | Weight, volume | mmol | Eq. |
|---|---|---|---|---|
| 2-butyl 1,3-diazaspiro[4.4]non-1-ene-3-(4-bromobenzyl)-4-one (IRB-05) | 363.3 | 0.96 g | 2.64 | 1.0 |
| IRB-07-THF-0.5 H$_2$O | 513.3 | 1.42 g | 2.77 | 1.05 |
| Pd(OAc)$_2$ | 224.49 | 5.7 mg | 0.026 | 1.15 |
| Triphenylphosphine | 262.5 | 27.3 mg | 0.104 | |
| 1,2-Dimethoxyethane | | 8 mL | | |

| | | -continued | | |
|---|---|---|---|---|
| THF | | 2 mL | | |
| Potassium carbonate | 138.21 | 0.912 g | 6.60 | 2.5 |
| Water | 18.0 | 0.119 mL | 6.60 | 2.5 |

A mixture of DME and THF was degassed by vacuum/nitrogen purges (3 times) and Ph₃P was added in one portion. After the triphenylphosphine dissolved, Pd(OAc)₂ was added, and the yellow-green mixture was degassed again (2 times), and stirred for 30 min at room temperature. IRB-07 was suspended, and stirring was continued for 10 min at room temperature. The water was added, and the slurry was stirred for additional 30 min. Powdered K₂CO₃ and IRB-05 were then added sequentially and the resulting mixture was degassed (3 times), and refluxed (approx. 80° C.) for 3 hours (TLC monitoring: Hex/EtOAc 2:1). The solvents were evaporated under reduced pressure, and toluene (20 mL) and water (20 mL) were added. After separation, the aqueous phase was extracted with toluene (10 mL) and the combined organic phases were washed with water and brine, dried over Na₂SO₄ and evaporated under reduced pressure to give 2.1 g of the semisolid residue. The crude material was crystallized from IPA (15 mL) to give 1.6 g of IRB-03 as a white solid. The yield was 90%, with a purity of 98%.

EXAMPLE 1E

Preparation of Irbesartan (IRB-00)

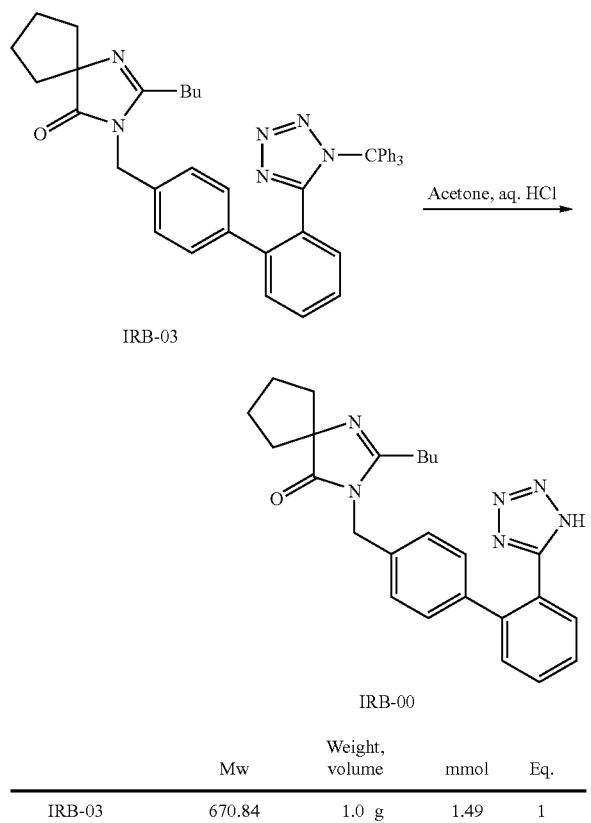

| | Mw | Weight, volume | mmol | Eq. |
|---|---|---|---|---|
| IRB-03 | 670.84 | 1.0 g | 1.49 | 1 |
| HCl, 3N | | 1.5 mL | 4.5 | 3 |
| Acetone | | 3 mL | | |
| KOH, 85% | 56.11 | 0.42 g | | 5 |

IRB-03 (as produced in Example 1D) was dissolved in acetone and 3N HCl, and stirred for 2 hours at room temperature (TLC or HPLC monitoring). A solution of KOH in 3 mL of water was slowly added, and acetone was evaporated under reduced pressure. The precipitate (Trityl alcohol) was filtered and washed with water (2×5 mL). The combined aqueous filtrate washed with 5 mL of ethyl acetate, and slowly acidified to pH 4 with 3N aqueous HCl. The resulting suspension was cooled down to 0–4° C., stirred for additional 30 min and filtered. The cake was washed several times with water and dried under reduced pressure at 50–60° C. The yield was 0.58 g of IRB-00.

We claim:

1. A process of making 2-butyl-3-[2'-(1-triphenylmethyl-1H-tetrazol-5-yl)-biphenyl-4-yl methyl]-1,3-diazaspiro[4.4]non-1-ene-4-one, comprising the step of reacting 2-butyl-3-(4-bromobenzyl)-1,3-diazaspiro[4.4]non-1-ene-4-one with 2-((1-trityl-1H-tetrazol-5-yl))phenylboronic acid in a solvent system comprising first and second solvents in the presence of a catalyst.

2. The process of claim 1, wherein the catalyst is selected from the group consisting of palladium complexes and a nickel complexes.

3. The process of claim 2, wherein the catalyst comprises a combination of a palladium complex and a triaryl phosphine.

4. The process of claim 3, wherein the palladium complex is Pd(OAc)₂ and the triaryl phosphine is triphenyl phosphine.

5. The process of claim 1, wherein the first solvent is selected from the group consisting of ethers, formals, hydrocarbons, the tetralins or mixtures thereof.

6. The process of claim 5, wherein the first solvent is selected from the group consisting of: dimethoxyethane (DME), diethoxymethane (diethyl formal), tetrahydrofuran, toluene, m-xylene and o-xylene.

7. The process of claim 6, wherein the first solvent is a mixture of dimethoxyethane and tetrahydrofuran.

8. The process of claim 7, wherein the ratio of dimethoxyethane to tetrahydrofuran is about 10:1 to about 1:5 on a volume basis.

9. The process of claim 8, wherein the ratio of dimethoxyethane to tetrahydrofuran is about 6:1 to about 2:1 on a volume basis.

10. The process of claim 1, wherein the second solvent comprises water and an inorganic base.

11. The process of claim 10, wherein the base is potassium carbonate.

12. The process of claim 1, wherein the reacting is at about reflux for a reaction time of about 2 hours to about 4 hours.

\* \* \* \* \*

UNITED STATES PATENT AND TRADEMARK OFFICE
CERTIFICATE OF CORRECTION

PATENT NO. : 7,217,825 B2 Page 1 of 1
APPLICATION NO. : 11/348945
DATED : May 15, 2007
INVENTOR(S) : Nisnevich et al.

It is certified that error appears in the above-identified patent and that said Letters Patent is hereby corrected as shown below:

Col. 10, lines 32-33, change "a nickel complexes" to --nickel complexes--.

Signed and Sealed this

Twenty-third Day of February, 2010

David J. Kappos
*Director of the United States Patent and Trademark Office*